United States Patent
Doerr et al.

(10) Patent No.: US 9,364,676 B2
(45) Date of Patent: Jun. 14, 2016

(54) BIVENTRICULAR CARDIAC STIMULATOR

(75) Inventors: Thomas Doerr, Berlin (DE); Torsten Radtke, Berlin (DE)

(73) Assignee: Biotronik CRM Patent AG (CH)

( * ) Notice: Subject to any disclaimer, the term of this patent is extended or adjusted under 35 U.S.C. 154(b) by 885 days.

(21) Appl. No.: 12/890,351

(22) Filed: Sep. 24, 2010

(65) Prior Publication Data

US 2011/0082512 A1    Apr. 7, 2011

Related U.S. Application Data

(60) Provisional application No. 61/249,260, filed on Oct. 7, 2009.

(51) Int. Cl.
*A61N 1/36* (2006.01)
*A61N 1/365* (2006.01)
*A61N 1/368* (2006.01)
*A61N 1/37* (2006.01)

(52) U.S. Cl.
CPC ........... *A61N 1/36514* (2013.01); *A61N 1/3684* (2013.01); *A61N 1/37* (2013.01)

(58) Field of Classification Search
CPC .... A61N 1/37; A61N 1/3684; A61N 1/36514
USPC .......................................................... 607/9
See application file for complete search history.

(56) References Cited

U.S. PATENT DOCUMENTS

| 6,493,586 | B1 | 12/2002 | Stahmann et al. | |
|---|---|---|---|---|
| 6,922,589 | B2 | 7/2005 | Stahmann et al. | |
| 2003/0153951 | A1* | 8/2003 | Ideker et al. | 607/3 |
| 2003/0176894 | A1* | 9/2003 | Stahmann et al. | 607/9 |
| 2004/0215256 | A1* | 10/2004 | Keizer et al. | 607/9 |
| 2005/0256547 | A1 | 11/2005 | Stahmann et al. | |
| 2008/0097536 | A1 | 4/2008 | Kramer et al. | |
| 2008/0306567 | A1 | 12/2008 | Park et al. | |
| 2009/0069858 | A1 | 3/2009 | Dong et al. | |

FOREIGN PATENT DOCUMENTS

WO    WO 02/18010 A2    3/2002

* cited by examiner

*Primary Examiner* — Alyssa M Alter
(74) *Attorney, Agent, or Firm* — Craig A. Fieschko, Esq.; DeWitt Ross & Stevens S.C.

(57) ABSTRACT

A biventricular cardiac stimulator has a right-ventricular sensing unit, having or connected to a terminal for a right-ventricular sensing electrode, a left-ventricular sensing unit, having or connected to a terminal for a left-ventricular sensing electrode, and a pacemaker timer, which is connected to the right-ventricular sensing unit and the left-ventricular sensing unit. The cardiac stimulator has a programmable automatic switch, which is effectively connected to the pacemaker timer to switch the pacemaker timer optionally between a primarily right-ventricular control and a primarily left-ventricular control, as well as an evaluation unit, which is effectively connected to the switch and is designed to detect and evaluate at least one stability parameter that is characteristic of the stability of the electrode position of the left-ventricular sensing electrode, whereby the programmable automatic switch is designed to automatically switch the pacemaker timer control as a function of a value of the detected stability parameter.

20 Claims, 7 Drawing Sheets

BIVENTRICULAR CARDIAC STIMULATOR

RELATED APPLICATION

This patent application claims the benefit of U.S. Provisional Patent Application No. 61/249,260, filed on Oct. 7, 2009, which is hereby incorporated by reference in its entirety.

TECHNICAL FIELD

The present disclosure relates to a biventricular cardiac stimulator having a right-ventricular sensing unit, a left-ventricular sensing unit, and a pacemaker timer, which determines points in time for delivering stimulation pulses, e.g., right-ventricular or left-ventricular stimulation pulses, among other things. The right-ventricular sensing unit is connected or connectable to a right-ventricular sensing electrode, while the left-ventricular sensing unit is accordingly connected or connectable to a left-ventricular sensing electrode.

BACKGROUND

Biventricular cardiac pacemakers are typically designed for stimulation of the right and left ventricles of the heart to perform cardiac resynchronization therapy (CRT), for example. To do so, a biventricular cardiac stimulator typically has a right-ventricular stimulation unit and a left-ventricular stimulation unit, each being connected or connectable to at least one right-ventricular and/or at least one left-ventricular stimulation electrode.

The right-ventricular sensing electrode(s) and the right-ventricular stimulation electrode(s) are typically attached to a right-ventricular electrode line, while the left-ventricular sensing electrode(s) and the left-ventricular stimulation electrode(s) are components of a left-ventricular electrode line. Such left-ventricular electrode lines are typically advanced through the coronary sinus into proximity to the left ventricle and therefore are also referred to as CS electrode lines. Left-ventricular electrode lines, in comparison with right-ventricular electrode lines, incur an increased probability that the electrode line will be shifted, which changes the sensing and stimulation conditions.

On the basis of stimulated or sensed events, a pacemaker timer determines points in time at which stimulation pulses are to be delivered to the respective chamber of the heart. A stimulated event is delivery of a stimulation pulse, which leads to a contraction of the respective chamber of the heart. A detected event, also known as a natural or intrinsic event, is an independent contraction of the corresponding chamber of the heart, which is detected by a corresponding sensing electrode. The corresponding sensing electrode detects the electric potentials associated with a natural contraction of a corresponding chamber of the heart. These potentials are amplified and evaluated by the pacemaker controller and, in particular, by the pacemaker timer.

As is known to those skilled in the art, a natural contraction of the right atrium can be detected as a so-called P wave portion of an electrocardiogram (ECG) signal. The corresponding intrinsic right-atrial event is referred to here as $A_s$ (atrium sense). The natural contraction of the right ventricle is manifested in the form of an R wave in an is electrocardiogram. A detected natural contraction of the right ventricle is referred to here as $RV_s$. A detected natural contraction of the left ventricle is referred to here as $LV_s$. $RV_p$ denotes a stimulated, or paced, event in the right ventricle. Accordingly, $LV_p$ denotes a stimulated, or paced, event in the left ventricle. It is known that cardiac stimulators generate a marker signal to identify the respective detected (natural) event or stimulated event, characterizing the point in time corresponding to the respective event. The pacemaker timer can then access these marker signals. Marker signals are frequently transmitted in a respective channel, e.g., a right-atrial detection channel, a right-ventricular detection channel or a left-ventricular detection channel.

In this context, it is known that the points in time for delivery of a respective stimulation pulse may be determined, but the delivery of a stimulation pulse is to be suppressed (to be inhibited) if an independent contraction of the respective chamber of the heart, (i.e., an intrinsic event of this chamber of the heart) is detected within a certain interval before the intended stimulation time. If the cardiac stimulator is designed in this way, it stimulates the respective chamber of the heart only on demand and therefore the corresponding mode of operation is also known as demand mode.

As already mentioned, the points in time at which the respective next stimulation pulse of a respective chamber is provided are determined by the pacemaker timer on the basis of sensed events or stimulated events. In a known manner, the pacemaker timer is designed so that the chambers of the heart contract in a chronological order as closely as possible to the action of a healthy heart as a function of the respective hemodynamic demand. For example, a contraction of the right atrium after an atrioventricular conduction time is followed by a contraction of the right ventricle. In a similar manner, the pacemaker timer determines the point in time for delivery of the next right-ventricular stimulation pulse on the basis of an atrioventricular delay time (AVD), which is triggered by a stimulated or detected event in the right atrium. The atrioventricular delay time is advantageously variable, such that the pacemaker timer is able to adapt optimally to the respective hemodynamic demand and to the individual needs of the respective patient.

In a cardiac pacemaker which stimulates both the right atrium and the right ventricle, the pacemaker timer also determines the point in time of the next atrial stimulation after a VA delay time, which follows the respective stimulated or detected ventricular event and depends is to a substantial extent on the heart rate, which is adapted as well as possible to the hemodynamic demand. A cardiac stimulator having a pacemaker timer which can adapt the stimulation rate to the hemodynamic demand is known as a rate-adaptive cardiac stimulator.

In biventricular cardiac stimulators, the left ventricle may additionally be stimulated to synchronize the actions (contractions) of the right ventricle and the left ventricle as part of a cardiac resynchronization therapy (CRT). In this context, an interventricular delay time (VVD) also plays a role for the pacemaker timer, because the VVD describes the time delay between the intended delivery of a right-ventricular stimulation pulse and the intended delivery of a left-ventricular stimulation pulse. The VVD may be zero or even negative so that, for example, delivery of a left-ventricular stimulation pulse prior to delivery of a right-ventricular stimulation pulse may be provided. This interventricular delay time is preferably variable, in the sense that the pacemaker timer can adjust to individual needs and instantaneous requirements of a respective patient.

Because it is known in the art that some biventricular cardiac stimulators are capable of also stimulating the right atrium, and therefore they are considered to be "triple-chamber stimulators," no further detailed description thereof need be given here.

SUMMARY

According to a preferred embodiment, improvement of a cardiac stimulator for cardiac resynchronization therapy may be achieved by a biventricular cardiac stimulator having a right-ventricular sensing unit, which has or is connected to a terminal for a right-ventricular sensing electrode; a left-ventricular sensing unit, which has or is connected to a terminal for a left-ventricular sensing electrode; and a pacemaker timer, which is connected to the right-ventricular sensing unit and the left-ventricular sensing unit, such that the cardiac stimulator has a programmable automatic switch, which is operatively connected to the pacemaker timer and is designed to switch the pacemaker timer optionally between a primarily right-ventricular control and a primarily left-ventricular control, as well as a detection unit, which is effectively connected to the switch and is designed to detect at least one stability parameter that is characteristic of the stability of the electrode position of the left-ventricular sensing unit, such that the programmable automatic switch is designed to automatically switch the pacemaker timer control as a function of a value of the stability parameter detected.

A primary feature of the novel biventricular cardiac stimulator is automatic switching to a primarily left-ventricular control. Primarily left-ventricular control means that the definitive event for pacemaker timing is derived from the left-ventricular sensing electrode. Thus, for example, in R-synchronous modes, the stimulation interval is initiated with a left-ventricular (LV) event. In P-synchronous modes, the VA time is initiated with a left-ventricular event.

The method described here for switching from primarily right-ventricular to primarily left-ventricular control can also be used for the opposite direction, e.g., when the left-ventricular sensing electrode no longer yields useful or stable signals due to an electrode breakage or dislocation.

The novel embodiments are based on the finding that the timing of biventricular stimulators (CRT systems) available at the present time is controlled via the right-ventricular sensing electrode and, if present, the right-atrial sensing electrode. Signals from the left-ventricular sensing electrode are used only for inhibition of a left-ventricular stimulation in the case of an intrinsic action of the left ventricle sensed there. The reason for cautious use of the left-ventricular signal is a higher dislocation rate of the left-ventricular electrode line, especially in the first weeks after implantation.

With the increasingly widespread use of CRT stimulators, however, there has been growing recognition of the fact that the signals of the left-ventricular sensing electrode are to be preferred for control of the pacemaker timer. This is generally possible when the position of the LV electrode line is evaluated as being stable (e.g., several weeks after implantation).

The example illustrated in FIG. 1 demonstrates a disadvantage of RV-controlled CTR stimulation. FIG. 1 shows the atrial (A), right-ventricular (RV) and left-ventricular (LV) marker channels. These include the surface ECG and the corresponding intracardiac electrograms. On the basis of a left-ventricular extrasystole (VES), the left ventricle contracts in prematurely. This stimulus is then conducted to the right ventricle. At the same time, the atrial timer counts down and initiates an atrial stimulation. This stimulation in the atrial channel starts a blanking interval in the neighboring sensing channels (RV and LV) during which no events are detected in these channels. Because of this blanking, the VES conducted from the left ventricle to the right ventricle cannot be detected. Because the right-ventricular is stimulus is not detected, after the programmed LV conduction time has elapsed, a right-ventricular stimulation is delivered. This stimulation occurs in the ascending T-wave (see ECG) and induces a ventricular tachycardia.

The switch is preferably a component of the pacemaker timer and is arranged and designed, so that the pacemaker timer, independently of the switch state of the switch, has access to signals originating from the right-ventricular electrode line as well as signals originating from the left-ventricular electrode line, so that the pacemaker time can make the control of the stimulation therapy depend on both signals. The switch then causes the pacemaker timer to switch off primarily at the signals of one of the two electrodes, as described in the introduction. At the same time, the pacemaker timer may also take into account events of the other channel respectively, e.g., for inhibition of stimulation pulses, in addition to events of the primary control channel.

In another preferred embodiment variant, in which the left-ventricular sensing unit has a left-ventricular ECG signal amplifier supplying a left-ventricular input signal for the evaluation unit, the evaluation unit is preferably designed to detect the maximum amplitude of the left-ventricular input signal as a stability parameter.

In a first subvariant, the evaluation unit is also designed to compare the value of the maximum amplitude of the left-ventricular input signal with a threshold value and to induce switching of the switch from primary right-ventricular control to primarily left-ventricular control (and preferably also vice versa) when the left-ventricular input signal exceeds the predefined threshold value at least once (or conversely falls below a minimum threshold value).

In this context, it is preferable if the evaluation unit is designed to induce switching of the switch only when the left-ventricular input signal exceeds the predefined threshold value of a predefined number (X) of times within a predefined number (Y) of cardiac cycles. It is possible in this way to preclude the fact that a random incident exceeds the threshold value from already triggering a switch from primarily right-ventricular control to primarily left-ventricular control.

In addition, it is preferable if the evaluation unit is also connected to a right-ventricular sensing unit of the biventricular cardiac stimulator, which has a right-ventricular ECG signal amplifier supplying a right-ventricular input signal for the evaluation unit. In this case, the evaluation unit is additionally designed to also detect the maximum amplitude of the right-ventricular input signal as an additional control parameter.

A preferred embodiment variant is one in which the evaluation unit compares the maximum amplitude of the respective left-ventricular input signal with the value of the maximum amplitude of the respective right-ventricular input signal and triggers a switching of the switch to a primarily left-ventricular control when the value of the maximum amplitude of the respective left-ventricular event is greater than the value of the maximum amplitude of the respective right-ventricular event. The evaluation unit thus makes an amplitude comparison and selects the input signal having the greater maximum amplitude for further control.

In addition, the evaluation unit may be designed to evaluate at least one morphological signal characteristic as an additional control parameter. Suitable morphological signal characteristics include, for example, the width of the QRS complex in the left-ventricular input signal, the slew rate of the left-ventricular input signal, the integral of a QRS complex in the left-ventricular input signal, and frequency contents of the left-ventricular input signal.

In the case of a cardiac stimulator that additionally has a right-atrial sensing unit, the evaluation unit is preferably also connected to this sensing unit, and the evaluation unit is designed to evaluate a chronological relationship between correlated right-atrial events and left atrial events as an additional stability parameter. This may be accomplished, for example, with the help of a histogram of a plurality of intervals between an intrinsic atrial event ($A_s$) and the respective intrinsic left-ventricular event ($LV_s$). Switching to primarily left-ventricular control may be accomplished, for example, when more than 95% of the intervals detected in the histogram are within a defined time range.

In an especially preferred embodiment variant, the evaluation unit is designed to make switching of the pacemaker timer control a function of three criteria, namely the maximum amplitude of the left-ventricular input signal, at least one morphological signal characteristic and the chronological relationship between the respective correlated right-atrial and left-ventricular events. The evaluation unit may be designed to induce switching to primarily left-ventricular control when at least two of these three criteria fulfill at least one predefined condition. Alternatively, the evaluation unit may also be designed to induce switching only when all three of these criteria also fulfill at least one predefined condition.

The pacemaker timer is preferably embodied to perform a parameter transformation when switching from primarily right-ventricular control to primarily left-ventricular control or vice versa to ensure that, with the parameter transformation, the chronological relationship between the events relevant for biventricular stimulation is maintained.

Other advantages are derived from the following description of preferred exemplary embodiments.

DESCRIPTION OF THE DRAWINGS

The present invention will now be explained in greater detail on the basis of an exemplary embodiment with reference to the figures, in which.

DETAILED DESCRIPTION

Figure 1:
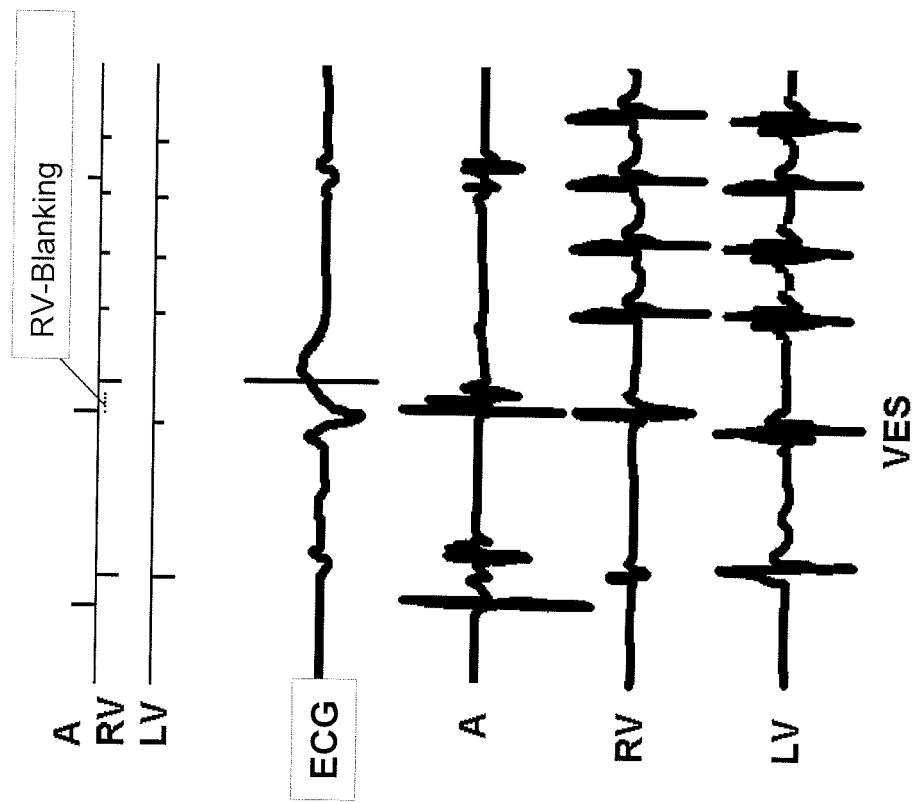
FIG. 1: shows a possible negative effect of primarily right-ventricular time control on the basis of an illustrative prior art example.
Figure 2:
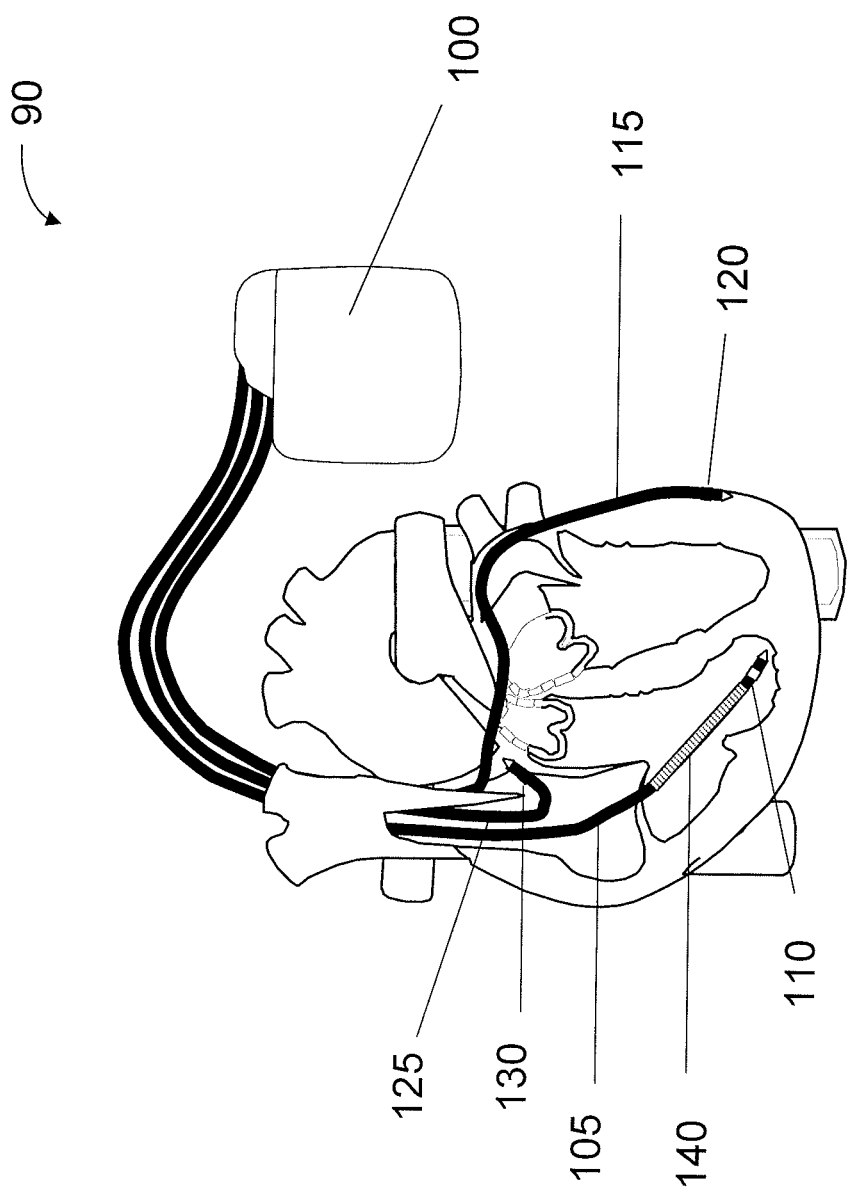
FIG. 2: shows a triple-chamber cardiac stimulator together with the connected electrode lines.

FIG. 2 shows a biventricular stimulation system 90 that includes a triple-chamber cardiac stimulator 100, which is connected by a right-ventricular electrode line 105 to an electrode 110 for right-Ventricular sensing and stimulation, by a left-ventricular line 115 to an electrode for left-ventricular sensing and stimulation 120, and optionally by a right-atrial electrode line 125 to an electrode for right-atrial sensing and stimulation 130. The right-ventricular electrode line 105 may optionally (if the cardiac stimulator 100 is designed as an implantable cardioverter/defibrillator (ICD)) be provided with a shock electrode 140 for delivering a defibrillation shock.

Figure 3:
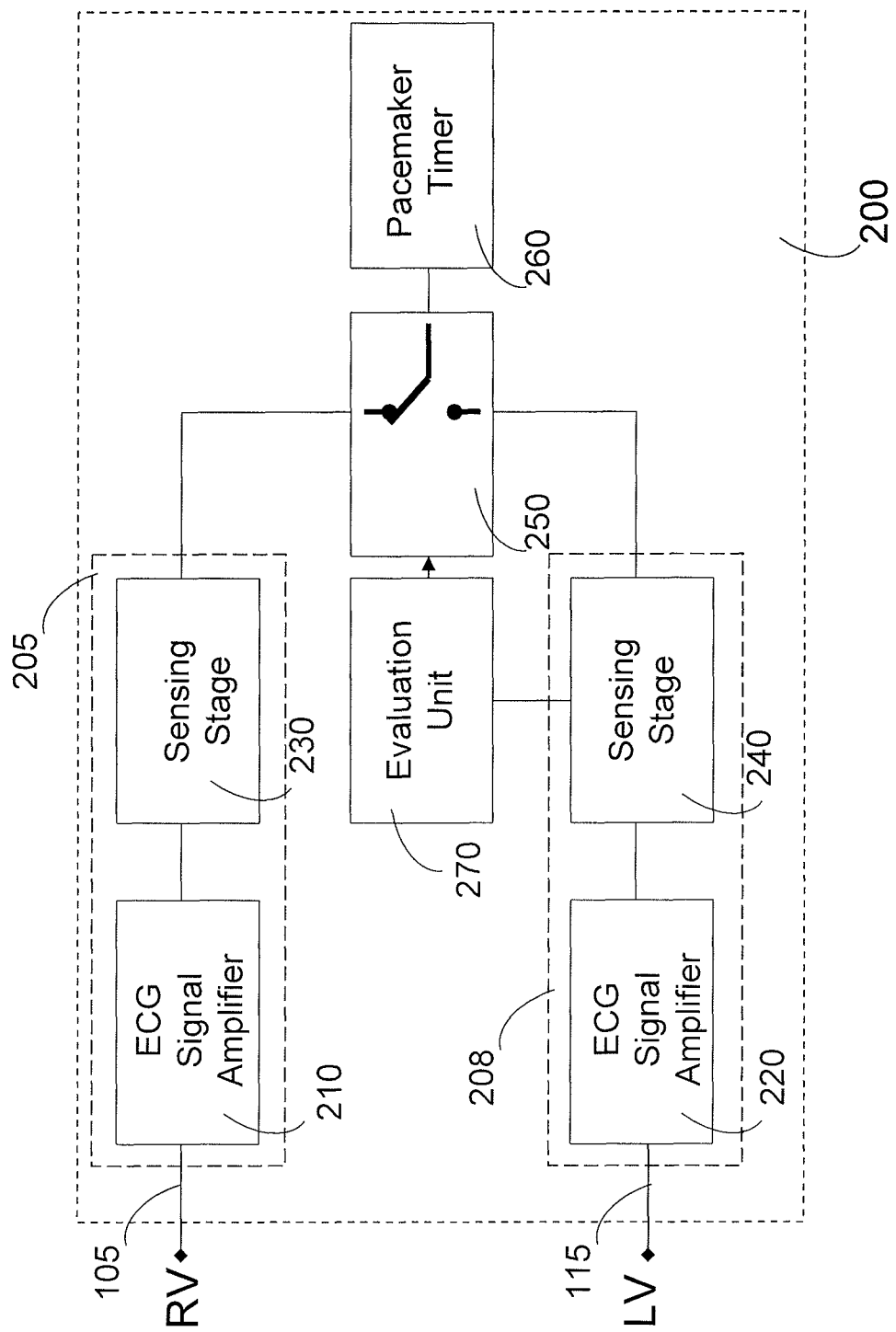
FIG. 3: shows a schematic block diagram of a few selected components of a biventricular cardiac stimulator such as that shown in FIG. 2 in a first variant.

FIG. 3 shows an excerpt of a block diagram of a biventricular, cardiac stimulator 200. This excerpt shows only the components of the exemplary embodiment that are relevant within the scope of the invention described here. The right-ventricular electrode line 105 and the left-ventricular electrode line 115 are each connected to a sensing unit 205 and 208, respectively, each of which contains an ECG signal amplifier, 210 and 220, respectively, and a sensing stage 230 and 240, respectively, connected to each signal amplifier. In the sensing stages 230 and 240, the point in time of ventricular stimulation is determined, e.g., by a threshold value comparison.

The sensing stages 230 and 240 are connected via a programmable switch 250 to a pacemaker timer 260. This switch 250 determines which event (RV or LV) is used to control the pacemaker timer 260. Switch 250 is controlled by an evaluation unit 270 for evaluating the stability of the electrode position of the left-ventricular electrode line 115. To do so, the switch 250 is connected at least to the ECG signal amplifier 220, which is connected to the left-ventricular electrode line 115 and receives the output signal of the ECG signal amplifier 220 as a left-ventricular input signal.

Stimulation units (not shown here), which can a) generate a stimulation pulse for a respective cardiac chamber in response to a signal of the pacemaker timer 260 and b) deliver it via the corresponding electrode line 105, 115, or 125, may be connected to the pacemaker timer 260 in the usual manner.

Figure 4:
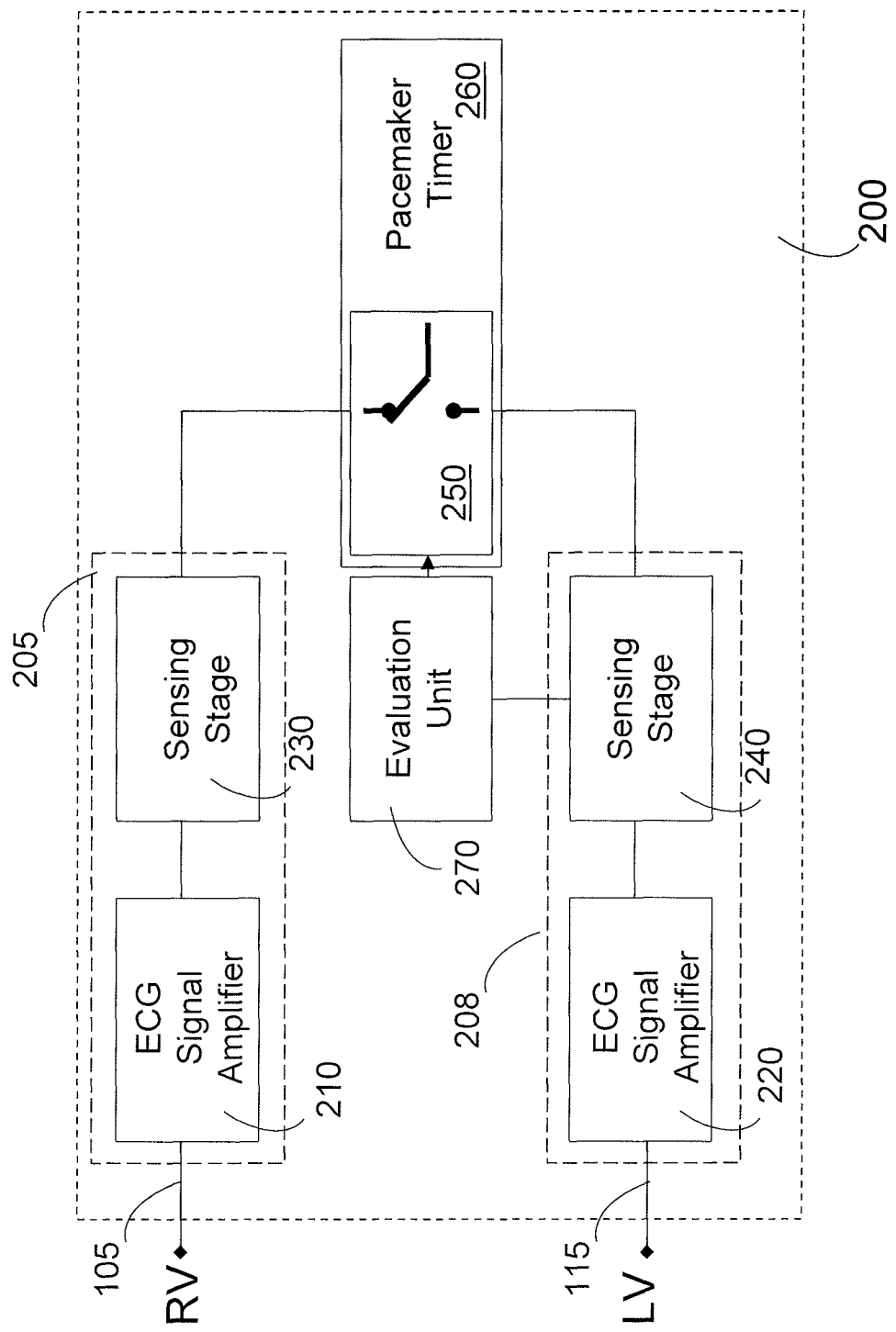
FIG. 4: shows a schematic block diagram of a few selected components of a biventricular cardiac stimulator such as that shown in FIG. 2 in a second variant.

According to a preferred embodiment variant, the switch 250 may be integrated into pacemaker timer 260 (see FIG. 4).

Figure 5:
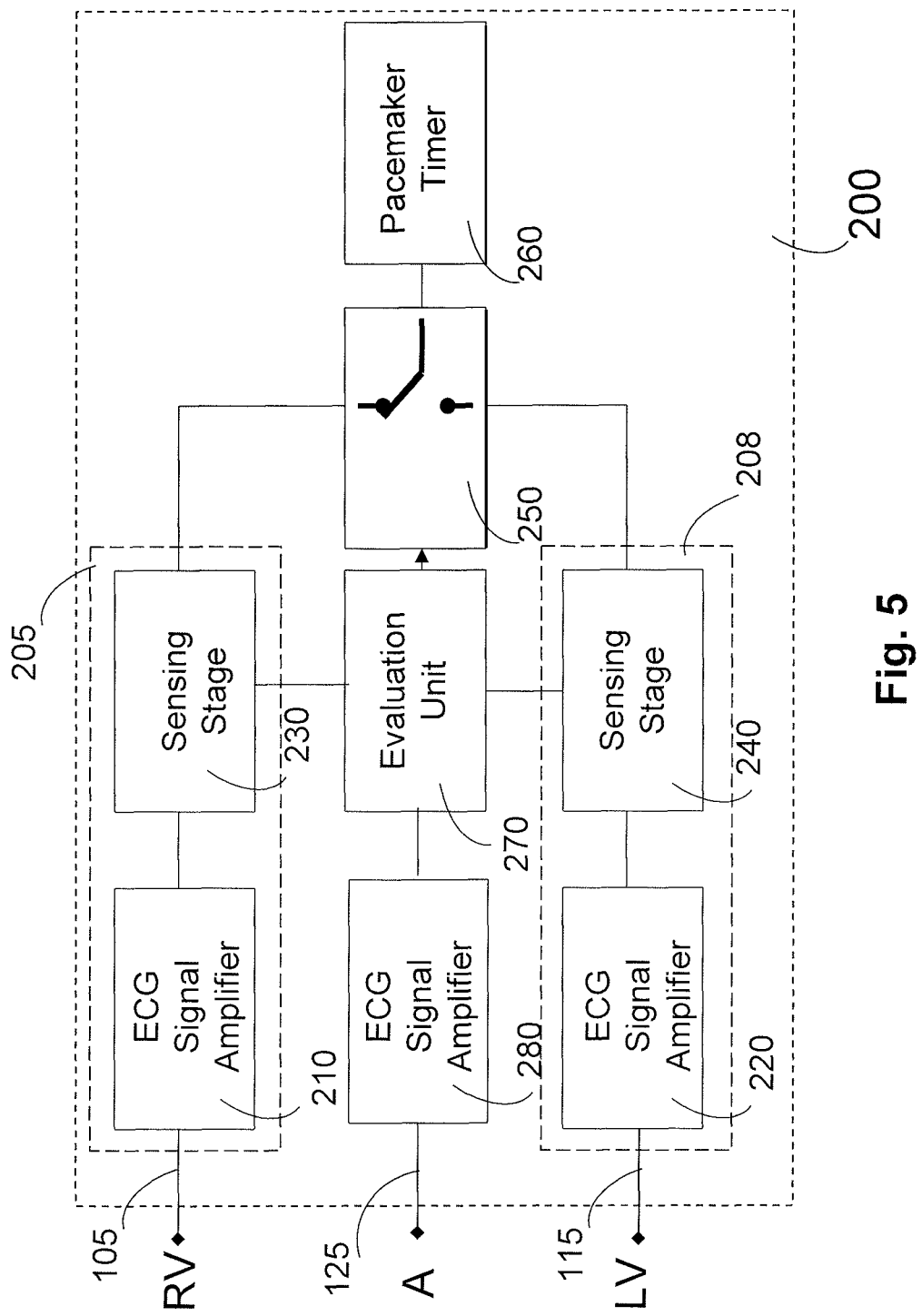
FIG. 5: shows a schematic block diagram of a few selected components of a biventricular chamber cardiac stimulator shown in FIG. 2 in a third variant.

Furthermore, evaluation unit 270 may be connected not only to the left-ventricular ECG signal amplifier 220 but also to the right-ventricular ECG signal amplifier 210 and to a right-atrial ECG signal amplifier 280, as diagrammed schematically in FIG. 5. This yields the possibility of taking into account other criteria for switching between primarily right-ventricular control and primarily left-ventricular control, as explained in greater detail below.

The block diagrams of biventricular stimulator 200 shown in FIGS. 3 to 5 may additionally be expanded by one or two atrial sensing channels. Likewise, in an embodiment of the cardiac stimulator implemented as an ICD, an additional arrhythmia classifier may also be provided, which is also switched optionally to the RV sensing stage 230 or the LV sensing stage 240 via a switch. In this case, the switching is preferably independent of the switching of the is pacemaker timer 260, so a second switch may additionally be provided upstream from the arrhythmia classifier.

However, the switching is preferably integrated into the pacemaker timer 260, so that first the signals of the right-ventricular electrode 110 and also those of the left-ventricular electrode line 115 are available to the pacemaker timer 260, but the switching influences the signal processing in the pacemaker timer 260. It is thus possible to also take into account the events of the other channel, respectively, e.g., for inhibition of stimulation pulses, in addition to taking into account events of the primary control channel.

Figure 6:
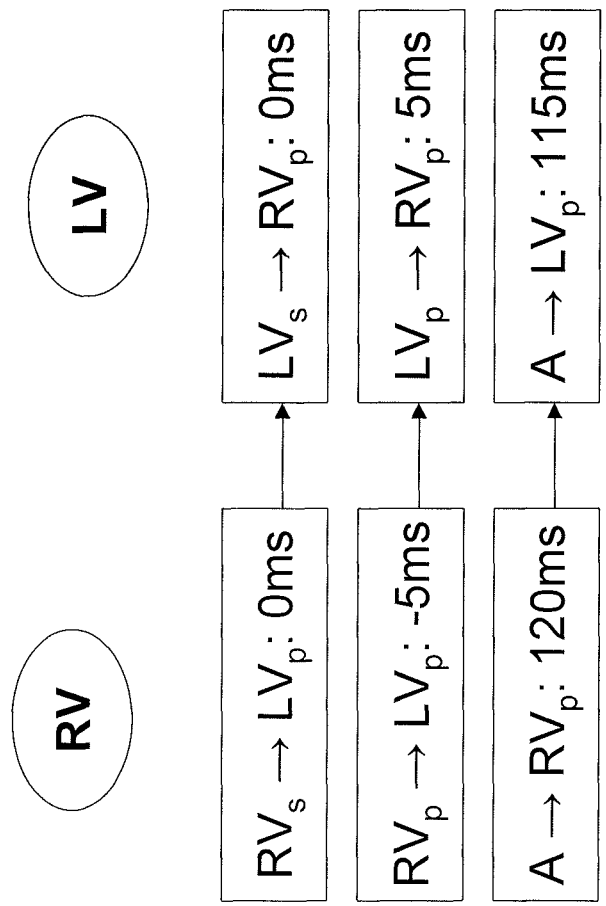
FIG. 6: shows an example of a parameter transformation in switching from a primarily RV-controlled timer to an LV-controlled timer.

FIG. 6 shows an example of a parameter transformation in switching from primarily right-ventricular control of the pacemaker timer 260 to primarily left-ventricular control. This parameter transformation ensures that the chronological relationships in the biventricular stimulation are still taken into account in the switching. Ideally, this parameter transformation is stored in a set of rules in the pacemaker tinier 260 or in a programming unit, so that this parameter adjustment can be used automatically in the switching.

In the case of primarily RV-controlled stimulation, the LV pacing stimulus ($LV_p$) is triggered as a function of the $RV_{sense}$ ($RV_s$) or the RV pacing stimulus ($RV_p$) with a corresponding VV time of, for example, about 5 ms. The RV pacing stimulus ($RV_p$) is initiated by an atrial event (A), delayed by a conduction time of about 120 ms.

Figure 7:
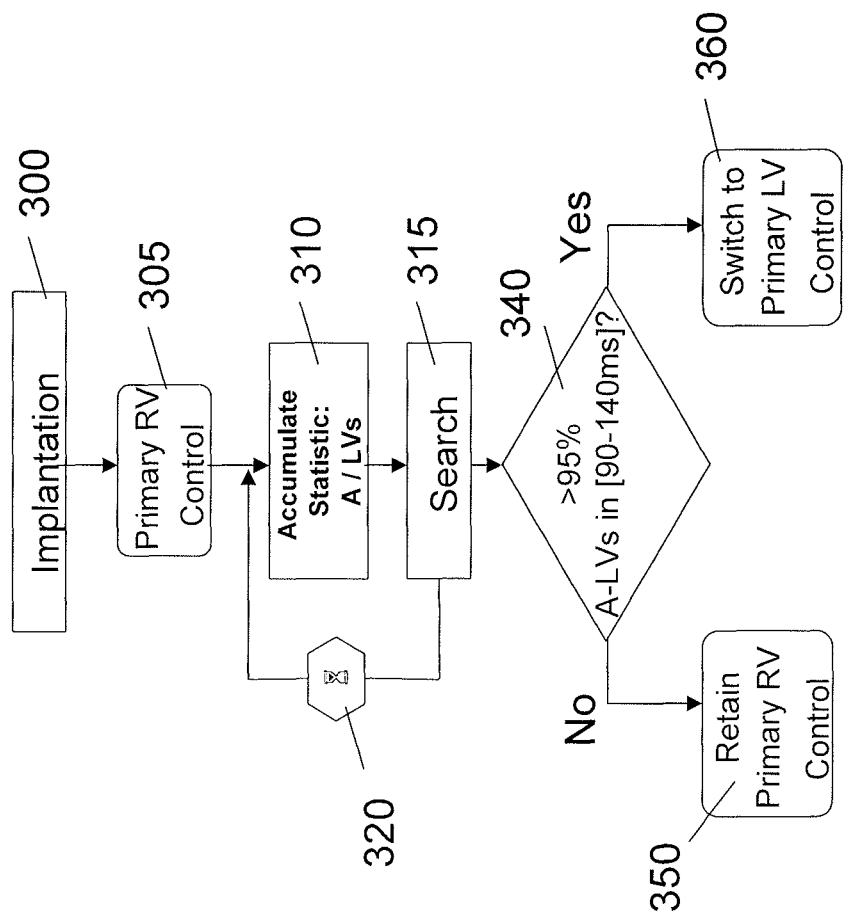
FIG. 7: shows an exemplary sequence of steps for automatic switching from primarily RV-controlled stimulation to primarily LV-controlled stimulation, after implantation.

If the biventricular stimulator 200 is then switched to a primarily LV-controlled pacemaker timer 260, then the timer parameters mentioned in the example shown in FIG. 6 are automatically transformed in the pacemaker timer 260. The right-ventricular stimulation ($RV_p$) then follows the left-ventricular event ($LV_s$ or $LV_p$), with the chronological relationship being transformed so that the actual stimulation moments in the transition from a primarily RV-controlled method to a primarily LV-controlled method remain unchanged. The same thing also holds for triggering of left-ventricular stimulation ($LV_p$). In this example, the AV conduction time is corrected by the VV delay (5 ms) accordingly:

FIG. 7 shows the sequence of an automatic switching from primarily RV-controlled stimulation to primarily LV-controlled stimulation after implantation 300 of stimulation system 90. Immediately after implantation 300 of the left-ventricular electrode line 115, the cardiac stimulator 200 is initially set to be, by default, primarily under RV control 305. To evaluate the stability of the left-ventricular electrode line 115, statistics of the left-ventricular events, based on the atrial events, are recorded in step 310. Recording of statistics may be implemented, e.g., by accumulating a histogram of the A-$LV_s$ times and by executing a search function 315 to detect intrinsic left-ventricular events. This recording is performed throughout a programmable time interval 320, e.g., for 12 weeks, to wait for ingrowth of the left-ventricular electrode line 115.

Once the time interval 320 has elapsed, a check is performed on whether the A-$LV_s$ statistics confirm a stable left-ventricular electrode position. This may be accomplished, for example, by checking in step 340 whether more than 95% of the recorded events occur within a defined time period 340, for example, a period within the range of 90-140 ms. If this is the case, then the system automatically switches to primary left-ventricular stimulation 360. If this condition is not met, then the system remains under primarily right-ventricular control 350.

In an expanded embodiment, alternate criteria may be used in decision step 340 in place of, or in addition to, the criteria set forth above, to evaluate the stability of the left-ventricular electrode 120. For example, the sensed left-ventricular signal amplitudes in a typical amplitude range may be checked against a threshold for left-ventricular signals (e.g., >8 mV). Or, X of Y measured left-ventricular amplitudes must reach a maximum value greater than 8 mV, and the minimum value must not be less than 3 mV. Furthermore, such an amplitude criterion may be supplemented by a comparison of the amplitude of the signal recorded in the right ventricle (right-ventricular amplitude) with the amplitude of the signal recorded in the left ventricle (left-ventricular amplitude). Switching to primarily left-ventricular control is performed only when the left-ventricular amplitude is greater than the right-ventricular amplitude.

A further improvement to the left-ventricular electrode stability evaluation depicted in FIG. 7 can be achieved by analysis of the morphological signal characteristics of the left-ventricular signal. For the morphological evaluation, an unfiltered signal derived in a parallel sensing channel is preferably evaluated. With an existing intrinsic rhythm (and/or with a search function for intrinsic events), the parameters QRS width in the left-ventricular signal, slew rate in the left-ventricular signal, integral of the QRS complex or the frequency contents of the left-ventricular signal may be evaluated for this purpose. In all these parameters, a left-ventricular signal is differentiated from an atrial signal, so that a good differentiation can be achieved and a left-ventricular electrode line that has been dislocated in the area of the atrium can be recognized easily.

For the morphology evaluation in stimulation, a method known from LV capture evaluation may be used. It is possible to differentiate very well regarding whether the LV electrode is in a stable implanted condition or whether it has been dislocated. In addition, the measured LV stimulus threshold may also be supplemented as a criterion. In other words, the position of the left-ventricular electrode line 115 is regarded as stable only when the stimulus threshold is within a predefined expectancy window.

To achieve good sensitivity and specificity for the left-ventricular electrode stability detection, all the aforementioned methods (A-LV time criterion, amplitude criterion and morphology criterion) may be combined as follows:

switching to a primarily left-ventricular control is performed when all three criteria are met;

switching back to a primarily right-ventricular control is performed when two of three criteria are no longer being met.

It will be apparent to those skilled in the art that numerous modifications and variations of the described examples and embodiments are possible in light of the above teaching. The disclosed examples and embodiments are presented for purposes of illustration only. Therefore, it is the intent to cover all such modifications and alternate embodiments as may come within the true scope of this invention.

What is claimed is:

1. A biventricular cardiac stimulator, comprising:

A.—a right-ventricular sensing unit, which has or is connected to a terminal for a right-ventricular sensing electrode, and which includes a right-ventricular ECG signal amplifier;

B.—a left-ventricular sensing unit, which has or is connected to a terminal for a left-ventricular sensing electrode; and C.—a pacemaker timer, which is connected to the right-ventricular sensing unit and the left-ventricular sensing unit, wherein the timer is characterized by (1)—a programmable automatic switch connected in communication with the pacemaker timer and configured to switch the pacemaker timer optionally between a primarily right-ventricular control and a primarily left-ventricular control; and (2)—an evaluation unit:

(a) connected to the switch;

(b) connected to the right-ventricular ECG signal amplifier and receiving a right-ventricular input signal supplied therefrom; and (c) configured to detect and evaluate one or more stability parameters that are characteristic of the stability of the electrode position of the left-ventricular sensing electrode, the stability parameters including:

(1) the maximum amplitude of a left-ventricular input signal obtained by the left-ventricular sensing unit; and (2) the maximum amplitude of the right-ventricular input signal, the programmable automatic switch further being configured to automatically switch the pacemaker timer control upon evaluating a value of the detected stability parameters which is indicative of improved stability of the electrode position of the left-ventricular sensing electrode.

2. The biventricular cardiac stimulator of claim 1 wherein the switch:
   a. is part of the pacemaker timer,
   b. is arranged and designed so that the signals of the right-ventricular electrode line as well as the signals of the left-ventricular electrode line are available to the pacemaker timer, and
   c. influences the signal processing in the pacemaker timer.

3. The biventricular cardiac stimulator of claim 1 wherein the evaluation unit is further configured:
   a. to compare the value of the maximum amplitude of a left-ventricular input signal with a threshold value, and
   b. to trigger switching of the switch when the left-ventricular input signal exceeds the predefined threshold value at least once.

4. The biventricular cardiac stimulator of claim 1 wherein the evaluation unit is further configured to trigger switching of the switch when the left-ventricular input signal exceeds the predefined threshold value a predefined number (X) of times within a predefined number (Y) of cardiac cycles.

5. The biventricular cardiac stimulator of claim 1 wherein the evaluation unit is further configured:
   a. to compare the value of the maximum amplitude of the respective left-ventricular input signal with the value of the maximum amplitude of the respective right-ventricular input signal and
   b. to trigger a switching of the switch to a primarily left-ventricular control when the value of the maximum amplitude of the respective left-ventricular input signal is greater than the value of the maximum amplitude of the respective right-ventricular input signal.

6. The biventricular cardiac stimulator of claim 1 wherein the pacemaker timer is designed to perform a parameter transformation when switching from primarily right-ventricular control to primarily left-ventricular control or vice versa, the parameter transformation being designed to maintain chronological relationships of the events relevant for a biventricular stimulation.

7. The biventricular cardiac stimulator of claim 1 wherein:
   a. —the programmable automatic switch is configured for primarily right-ventricular control as a default; and
   b. —the programmable automatic switch is configured to automatically switch the pacemaker timer control to primarily left-ventricular control when a value of one of the detected stability parameters is indicative of improved stability of the electrode position of the left-ventricular sensing electrode.

8. The biventricular cardiac stimulator of claim 1 wherein the programmable automatic switch is configured to automatically switch the pacemaker timer control to primarily left-ventricular control when
   a. —a value of one of the detected stability parameters is indicative of improved stability of the electrode position of the left-ventricular sensing electrode, and
   b. —the evaluation unit further detects that the stability of the electrode position of the right-ventricular sensing electrode is unchanged or improving.

9. The biventricular cardiac stimulator of claim 1 wherein the evaluation unit is further configured to detect and evaluate a morphological signal characteristic of the left-ventricular input signal as an additional stability parameter.

10. The biventricular cardiac stimulator of claim 9 wherein the evaluation unit is configured to detect and evaluate, as the morphological signal characteristic, one or more of:
   a. width of a QRS complex in the left-ventricular input signal,
   b. slew rate of the left-ventricular input signal,
   c. integral of a QRS complex in the left-ventricular input signal, and
   d. frequency contents of the left-ventricular input signal.

11. The biventricular cardiac stimulator of claim 1:
   a. further including a right-atrial sensing unit having or being connected to a terminal for a right-atrial sensing electrode,
   b. wherein the evaluation unit is:
      (1) additionally connected to the right-atrial sensing unit, and
      (2) further configured to evaluate a chronological relationship between correlated right-atrial events and left atrial events as an additional stability parameter.

12. The biventricular cardiac stimulator of claim 11 wherein the evaluation unit is further configured to detect and evaluate at least one morphological signal characteristic of the left-ventricular input signal as an additional stability parameter.

13. A biventricular cardiac stimulator including:
   a. a right-ventricular sensing unit having or being connected to a terminal for a right-ventricular sensing electrode, the right-ventricular sensing unit being configured to detect a right-ventricular input signal representing right-ventricular events;
   b. a left-ventricular sensing unit having or being connected to a terminal for a left-ventricular sensing electrode, the left-ventricular sensing unit being configured to detect a left-ventricular input signal representing left-ventricular events;
   c. a pacemaker timer connected to the right-ventricular sensing unit and the left-ventricular sensing unit;
   d. a programmable automatic switch:
      (1) connected in communication with the pacemaker timer, and
      (2) configured to switch the pacemaker timer optionally between a primarily right-ventricular control and a primarily left-ventricular control; and
   e. an evaluation unit:
      (1) connected in communication with the switch, and
      (2) configured to detect and evaluate one or more stability parameters that are characteristic of the stability of the electrode position of the left-ventricular sensing electrode, the stability parameters including:
         i. the maximum amplitude of a left-ventricular input signal obtained by the left-ventricular sensing unit, and
         ii. at least one morphological signal characteristic of the left-ventricular input signal;
   the programmable automatic switch further being configured to automatically switch the pacemaker timer control upon evaluating a value of the detected stability parameters which is indicative of improved stability of the electrode position of the left-ventricular sensing electrode.

14. The biventricular cardiac stimulator of claim 13 wherein the evaluation unit is configured to detect and evaluate, as a morphological signal characteristic, one or more signal characteristics from the group: width of a QRS complex in the left-ventricular input signal, slew rate of the left-ventricular input signal, integral of a QRS complex in the left-ventricular input signal and frequency contents of the left-ventricular input signal.

15. The biventricular cardiac stimulator of claim 13 wherein the evaluation unit is further configured to detect the maximum amplitude of the right-ventricular input signal as an additional stability parameter.

16. The biventricular cardiac stimulator of claim 13 wherein the evaluation unit is further configured to detect a chronological relationship between correlated right-atrial events and left atrial events as an additional stability parameter.

17. A biventricular cardiac stimulator including:
  a. a right-ventricular sensing unit having or being connected to a terminal for a right-ventricular sensing electrode, the right-ventricular sensing unit being configured to detect right-ventricular events;
  b. a right-atrial sensing unit having or being connected to a terminal for a right-atrial sensing electrode, the right-atrial sensing unit being configured to detect right-atrial events;
  c. a left-ventricular sensing unit having or being connected to a terminal for a left-ventricular sensing electrode, the left-ventricular sensing unit being configured to detect left-ventricular events;
  d. a pacemaker timer connected to the sensing units;
  e. a programmable automatic switch:
    (1) connected in communication with the pacemaker timer, and
    (2) configured to switch the pacemaker timer optionally between a primarily right-ventricular control and a primarily left-ventricular control; and
  f. an evaluation unit:
    (1) connected in communication with the switch, and
    (2) configured to detect and evaluate one or more stability parameters that are characteristic of the stability of the electrode position of the left-ventricular sensing electrode, the stability parameters including:
      i. the maximum amplitude of a left-ventricular input signal obtained by the left-ventricular sensing unit, and
      ii. a chronological relationship between mutually assigned right-atrial events and left atrial events,
  the programmable automatic switch further being configured to automatically switch the pacemaker timer control upon evaluating a value of the detected stability parameters which is indicative of improved stability of the electrode position of the left-ventricular sensing electrode.

18. The biventricular cardiac stimulator of claim 17 wherein the evaluation unit is configured to induce switching of the pacemaker timer control when at least two of the following criteria are met:
  a.—the maximum amplitude of the left-ventricular input signal satisfies at least one predefined condition;
  b.—at least one morphological signal characteristic satisfies at least one predefined condition; and
  b.—the chronological relationship between mutually assigned right-atrial events and left-ventricular events satisfies at least one predefined condition.

19. The biventricular cardiac stimulator of claim 17 wherein the evaluation unit is further configured to detect the maximum amplitude of the right-ventricular input signal as an additional stability parameter.

20. The biventricular cardiac stimulator of claim 17 wherein the evaluation unit is further configured to detect one or more morphological signal characteristics of the left-ventricular input signal as an additional stability parameter, the morphological signal characteristics including:
  a. width of a QRS complex in the left-ventricular input signal,
  b. slew rate of the left-ventricular input signal,
  c. integral of a QRS complex in the left-ventricular input signal, and
  d. frequency contents of the left-ventricular input signal.

* * * * *